United States Patent [19]

Wolinsky et al.

[11] Patent Number: 5,087,244
[45] Date of Patent: Feb. 11, 1992

[54] CATHETER AND METHOD FOR LOCALLY APPLYING MEDICATION TO THE WALL OF A BLOOD VESSEL OR OTHER BODY LUMEN

[75] Inventors: Harvey Wolinsky, New York, N.Y.; Spencer L. King, Atlanta, Ga.; Michael D. Barbere, Dunstable, Mass.

[73] Assignee: C. R. Bard, Inc., Murray Hill, N.J.

[21] Appl. No.: 590,048

[22] Filed: Sep. 27, 1990

Related U.S. Application Data

[63] Continuation of Ser. No. 304,352, Jan. 31, 1989, abandoned.

[51] Int. Cl.$^5$ .............................. A61M 29/00
[52] U.S. Cl. ....................... 604/53; 604/96; 604/99; 606/194
[58] Field of Search ................ 604/96-103, 604/93, 265, 51-56, 246; 128/207.15; 606/192, 194

[56] References Cited

U.S. PATENT DOCUMENTS

| | | | |
|---|---|---|---|
| 797,676 | 8/1905 | Flowers | 604/96 |
| 3,173,418 | 3/1965 | Baran | 128/202.15 |
| 3,981,299 | 9/1976 | Murray | 128/349 B |
| 4,211,233 | 7/1980 | Lin | 128/349 B |
| 4,323,071 | 4/1982 | Simpson et al. | 604/53 X |
| 4,327,721 | 5/1982 | Goldin et al. | 128/207.15 |
| 4,417,576 | 11/1983 | Baran | 128/207.15 |
| 4,423,725 | 1/1984 | Baron et al. | 128/207.15 |
| 4,437,856 | 3/1984 | Valli | 604/96 |
| 4,636,195 | 1/1987 | Wolinsky | 604/101 |
| 4,693,243 | 9/1987 | Buras | 128/207.15 |
| 4,782,834 | 11/1988 | Maguire | 604/96 |
| 4,821,722 | 4/1989 | Miller et al. | |
| 4,917,666 | 4/1990 | Solar et al. | 604/95 |
| 4,994,033 | 2/1991 | Shockey et al. | 604/101 |

FOREIGN PATENT DOCUMENTS 8912478 12/1989 PCT Int'l Appl.

*Primary Examiner*—John D. Yasko
*Assistant Examiner*—Adam Cermak
*Attorney, Agent, or Firm*—Morgan & Finnegan

[57] ABSTRACT

A method and catheter for use in practicing the method are provided by which a highly concentrated medication or chemotherapeutic agent can be applied locally under sufficient pressure to cause the medication or agent to penetrate into the localized tissue. The total volume of medication or agent is quite small, well below levels that might cause an adverse reaction in other parts of the body. The catheter includes a thin walled flexible balloon having a plurality of minute holes through which medication may flow at a low flow rate. The balloon is inflated with the medication under pressure and the flow rate of the order of a few ccs per minute is controlled by the minute holes in the balloon. In practicing the method of the invention, the balloon is selected such that its inflated diameter will correspond to or be slightly greater than the diameter of the lumen into which it is to be placed so that when the balloon is inflated, it will contact intimately the surface of the lumen. Inflation of the balloon with the medication will cause a thin film to spread between the balloon and the lumen, the film being maintained under a sufficient pressure to penetrate significantly the surrounding tissue with a high concentration of medication. The quantity of medication that ultimately flows free into the lumen is quite small and is insufficient to cause any other damage to the patient.

21 Claims, 2 Drawing Sheets

CATHETER AND METHOD FOR LOCALLY APPLYING MEDICATION TO THE WALL OF A BLOOD VESSEL OR OTHER BODY LUMEN

This application is a continuation of now abandoned parent application Ser. No. 304,352 filed Jan. 31, 1989, now abandoned.

FIELD OF THE INVENTION

The invention relates to catheter techniques for treating, with medicine, drugs or the like, a blood vessel or other body organ having a lumen through which the blood vessel or organ may be accessed.

BACKGROUND OF THE INVENTION

Often, in the treatment of various diseases, it may be desirable to treat a body organ, blood vessel or the like with medicine or drugs in a high concentration. Although desirable, the practice often may not be achievable because in order to apply the potentially toxic medicament in a sufficiently high dose to be effective in the region to be treated, the body may become flooded with dangerously high levels of the medicament which could result in damage to other parts of the body or could even be life threatening. For example, it has been found experimentally in animals that very high concentrations of heparin (or a particular component of heparin) when infused into the blood circulation tend to inhibit smooth muscle cell proliferation. See "Inhibition of Rat Arterial Smooth Muscle Cell Proliferation by Heparin" by John R. Guyton, et al., *Circulation Research*, Vol. 46, No. 5, May 1980, pp. 625-633; and "Vascular Smooth Muscle Proliferation Following Balloon Injury is Synergistically Inhibited by Low Molecular Weight Heparin and Hydrocortisone", John V. Gordon, et al., *Circulation* 76:IV-213, 1987. This may be of significance in connection with percutaneous transluminal angioplasty procedures by which an arterial stenosis is expanded to restore blood flow through an artery. Among the significant problems currently facing physicians practising angioplasty is that there is a relatively high rate of restenosis (of the order of 30%) after performing the initial angioplasty. It is believed that a significant contributing factor to restenosis may be smooth muscle cell proliferation of the artery wall. See "Intimal Proliferation of Smooth Muscle Cells as an Explanation for Recurrent Coronary Artery Stenosis After Percutaneous Transluminal Coronary Angioplasty" by Garth E. Austin, et al., *Journal American College of Cardiology*, Vol. 6, No. 2, August 1985, pp. 369-375. Thus, it may be advantageous to apply concentrated doses of heparin to an arterial wall that has been treated with angioplasty since effective doses of the heparin would be dangerous if introduced into the general circulation.

Although the desirability of applying high doses of medication to a local region of an artery or other body vessel has been recognized (see applicant's copending application Ser. No. 042,569 filed Apr. 21, 1987, now U.S. Pat. No. 4,824,432, and U.S. Pat. No. 4,423,725 issued Jan. 3, 1984 to Baran), there remains a need for an improved catheter for delivering such high concentrations without also flooding the patient's system with an unacceptably large concentration of the medication.

It is among the general objects of the invention to provide a method and apparatus for delivering high concentrations of medication to a localized area of a body vessel and to apply such medicine under pressure to cause penetration of the medicine into the wall of the body vessel, but without delivering large doses of the medication to the patient's overall system.

SUMMARY OF THE INVENTION

The invention involves the use of a balloon catheter having a flexible, inelastic cylindrical balloon at its distal end, the balloon having a plurality of regularly spaced minute openings through which medication may weep at a controlled, low flow rate. The balloon interior communicates with an inflation lumen extending through the shaft of the catheter and a fitting at the proximal end of the catheter for communicating the inflation lumen with a syringe or other pressure infusion device. The flow area defined by the perforations in the balloon is selected to provide a very low, weeping flow rate, typically of the order of a few cubic centimeters per minute through the balloon wall, the maximum flow rate depending on the particular medicine or drug being delivered. The catheter is selected with respect to the diameter of the lumen in the body vessel to be treated so that the inflated diameter of the balloon is slightly greater than the lumen diameter. Thus, when the balloon is inflated within the lumen it will press firmly against the surface of the body lumen. Once the balloon has been inflated by the medication solution, continued pressure applied to the interior of the balloon will force the medication through the perforations and between the balloon and the luminal surface of the body vessel. The medication spreads between the balloon and the body lumen, forming a thin film. The film is maintained under pressure by continually pressurizing the fluid in the catheter and the balloon, thereby causing medication to flow at a low weeping flow rate that is equal to or less than the maximum flow rate permitted by the minute balloon perforations. The continued pressure of the film forces the high dose medication to penetrate the wall of tissue defininq the body lumen while excess fluid bleeds off into the patient's system but at such a low volume that no adverse effect on other body organs or systems results. Such a film pressure may be maintained for up to several minutes to cause the medication to penetrate the tissue to the extent desired without introducing into the patient's system a large quantity of drugs.

It is among the objects of the invention to provide a catheter for local treatment, with a high concentration of medication or drugs, of a body member having a lumen, without exposing other parts of the body to such a high concentration of the medication or drug.

Another object of the invention is to provide a method for local treatment of a body vessel with a high concentration of medicine or drugs.

A further object of the invention is to provide a catheter having a perforated balloon adapted to permit fluid to weep through the balloon wall but at a low flow rate but no greater than a predetermined maximum rate.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
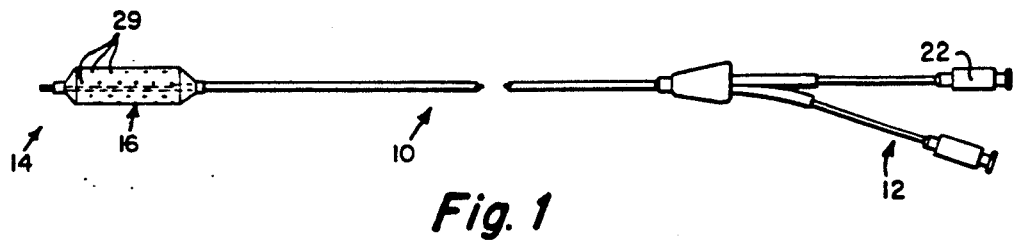
FIG. 1 is an illustration of the balloon catheter used in the practice of the invention.
Figure 2:
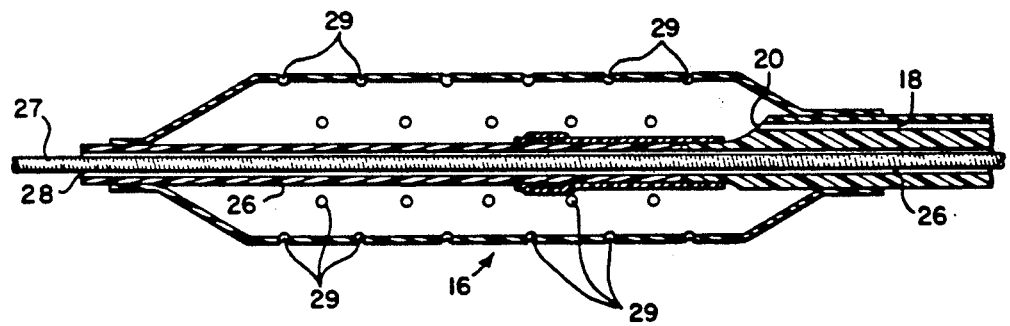
FIG. 2 is an enlarged longitudinal cross-sectional illustration of the catheter taken through the region of the balloon as seen along the line 2—2 of FIG. 1.

FIG. 1 illustrates the catheter used in the practice of the invention. The catheter includes an elongate flexible shaft 10 that may be formed in an extrusion process from an appropriate plastic material such as polyethylene. By way of example, when the catheter is intended to be used in the coronary arteries, the shaft may be of the order of 150 cm long and may have an outer diameter of 0.054". The catheter has a proximal end 12 and a distal end 14. An inflatable and deflatable balloon, indicated generally at 16 is mounted on the distal end 14 of the catheter shaft 10. As shown in FIG. 2, the catheter shaft 10 includes an inflation lumen 18 that extends from the proximal end of the shaft and terminates in an opening 20 within the balloon 16. The proximal end 12 of the catheter shaft 10 carries a fitting 22 by which the inflation lumen 18 may be connected to a syringe (not shown) or other pressure fluid delivery device. The catheter shaft 10 also may be formed to include a guidewire lumen 26 that extends to and terminates in an outlet orifice 28 at the distal tip of the catheter shaft 10. The guidewire lumen 26 may be used to receive a guidewire 27 by which the catheter may be guided through a patient's vasculature to the site to be treated.

Figure 3:
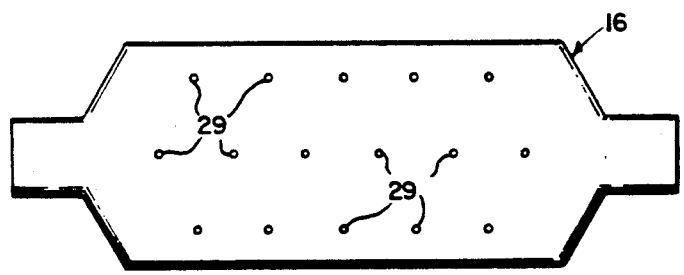
FIG. 3 is an illustration of the balloon laid flat showing the locations of holes as they may be formed by a laser.
Figure 4:
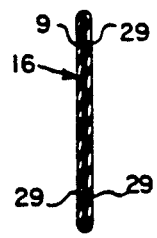
FIG. 4 is a side view of the flattened balloon as seen from an end thereof.
Figure 5:
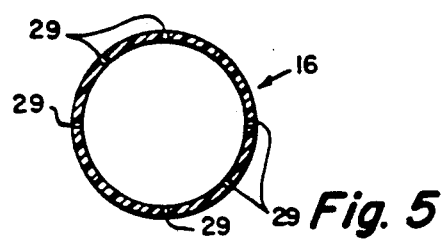
FIG. 5 is a sectional illustration through the balloon illustrating the circumferential spacing of the rows of holes.

The balloon 16 may be formed from various polymeric materials and desirably has a thin, flexible, preferably inelastic wall. A preferred material is polyethylene terephthalate and a balloon having a wall thickness of 0.001" or less may be fabricated as described in U.S. Pat. No. 4,490,421 (Levy) or U.S. Pat. application Ser. No. 001,759 filed Jan. 9, 1987 now abandoned (Saab). By way of example, a catheter according to the invention adapted for use in the coronary arteries may have a balloon about 20 mm or more long and a wall thickness of 0.001" or less. It is contemplated that with a relatively inelastic balloon several different sizes of (inflated) balloons may be required, depending on the application in which the catheter is to be used. For example, when used as an adjunct to angioplasty of the coronary arteries, balloons having diameters of 2.0 mm, 2.5 mm, 3.0 mm, 3.5 mm may be appropriate. In general, in connection with arterial angioplasty, it is contemplated that the balloon of the present invention should be selected to match the balloon used in the angioplasty procedure, the foregoing range being typical of the balloon sizes commonly employed in coronary angioplasty catheters. The balloon 16 is provided with a plurality of minute holes 29 that are substantially regularly spaced about the balloon 16. For example, we have found that an array of about thirty holes, each about 25 microns in diameter has been satisfactory. The holes may be formed by a laser beam from an excimer laser having wavelengths of 248 or 308 nm. These have been found to form clean edged holes in the balloon material. FIGS. 2 and 3 illustrate a satisfactory pattern of holes including six longitudinally extending rows having five holes 30 in each row. Some of the rows may be staggered longitudinally, with respect to each other as illustrated in FIG. 2. The holes are formed before the balloon is mounted on the catheter shaft. The balloon is laid flat as shown in FIGS. 4 and 5 while a laser beam is used to drill the holes 29 in the desired pattern shown. In that pattern, the holes extend over a length of about 12 mm of the balloon and are located on 1.2 mm centers for a 3.0 mm diameter balloon. The aggregate flow area defined by the holes 29 is selected so that under the general range of inflation pressures expected, the liquid flow through the holes will be very low, weeping in nature, and will not exceed a predetermined maximum flow rate in atmosphere. Although the foregoing configuration of holes is believed to be satisfactory for a wide range, and possibly most, if not all, medications or drugs to be delivered, it is possible that certain medications or drubs may have viscosity and flow characteristics as might require modification to the holes. The foregoing array of holes has been found to produce satisfactorily low flow rates for fluid medications having a viscosity and fluid characteristic similar to saline (such as heparin). In accordance with the invention, the maximum flow rate may be between about 2 to 12 cc per minute under inflation pressures of the order of 2 to 5 atmospheres. Additionally, it is important that the holes 29 do not define a flow area so large as would impair the ability of the balloon to be collapsed when the inflation lumen is aspirated. The flow area should be not so large that there is a significant fluid loss to any side branches that the balloon may be inflated across. This is after all the original problem with double balloon catheters and solved by the instant invention. Collapse of the balloon is necessary in order to permit the balloon to be withdrawn from the patient's vasculature.

Figure 6:
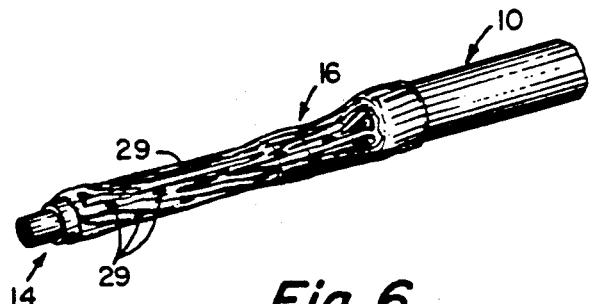
FIG. 6 is an illustration of the balloon in a deflated condition prior to insertion of the balloon into a patient's artery.
Figure 7:
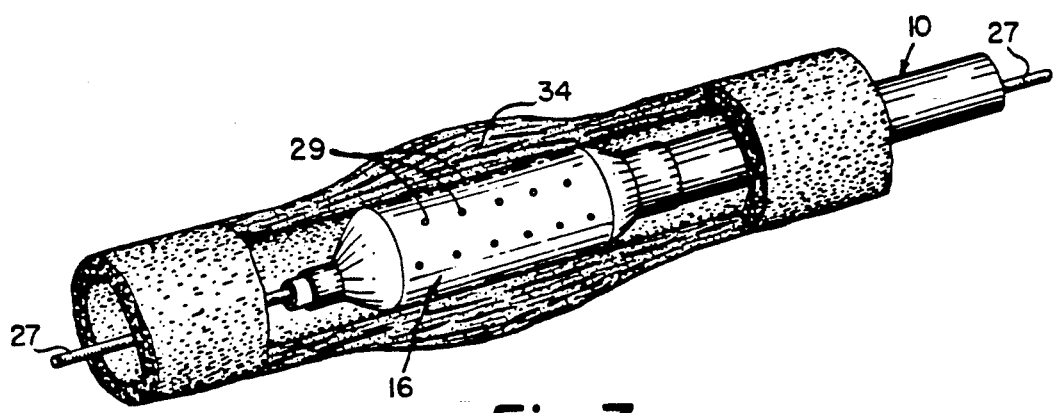
FIG. 7 is an enlarged illustration of the balloon portion of the catheter in an artery and in an inflated configuration.
Figure 8:
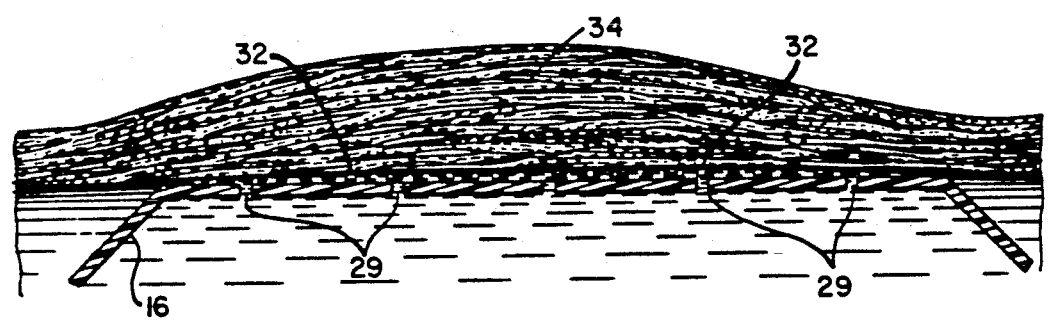
FIG. 8 is an enlarged cross-sectional illustration of the boundary region of the balloon, fluid film and artery.

Use of the catheter and practice of the method may be illustrated in arterial angioplasty, such as percutaneous transluminal coronary angioplasty. Typically, the angioplasty procedure will have been performed by the physician according to any of a variety of techniques using various angioplasty catheters available. For purposes of illustration, it may be assumed that the angioplasty procedure will have been performed either by a balloon catheter, laser catheter or other angioplasty catheter to enlarge the stenosed region to a luminal diameter of 2.5 mm. Typically, the arterial wall will display a certain amount of "recoil" after the angioplasty so that the luminal diameter may be slightly smaller than 2.5 mm. In order thereafter to treat the arterial wall with concentrated heparin (or an isolated heparin fraction having antiproliferative effect), the angioplasty catheter is removed from the patient, typically permitting the guidewire to remain in place. The catheter of the present invention will have been prepared, as by the physician's assistant, to fill the inflation lumen 18 and interior of the balloon 16 with the medication, taking care to purge the inflation and balloon system of air. The balloon then is wrapped about the catheter shaft to collapse the balloon to a low profile, as suggested by FIG. 6, by which it may be passed through the artery (or a quiding catheter leading to the coronary artery to be treated). The catheter then is advanced over the quidewire which guides the catheter to the site of the angioplasty. The catheter preferably is provided with one or more radiopaque marker bands by which the balloon position may be monitored under fluoroscopy to verify placement of the balloon in the region to be treated. Once the balloon is positioned within the site of the angioplasty, the syringe or other inflation device is operated to pressurize the catheter lumen and interior of the balloon to cause the balloon to inflate as suqgested in FIG. 7. By proper selection of the balloon size, the balloon will inflate into close pressing contact with the inner surface of the arterial lumen, effecting intimate surface contact with the lumen. Pressure is applied continually at the inflation device (which may be fitted with a pressure gauge) to maintain a substantially constant pressure level as desired, the range of pressures anticipated being of the order to 2 to 5 atmospheres. The pressure is sufficient to press the balloon firmly against the luminal surface of the artery but not so great as to preclude medication from weeping through the holes 30 in the balloon. As the medication weeps through the holes, it spreads into a generally cylindrical film 32 between the balloon 16 and artery wall 34. Because of the tendency of the balloon to intimately contact the artery wall, the film 32 will be maintained under pressure and will be forced into the arterial wall. Although there is some fluid pressure drop as the fluid weeps through the holes 29 and between the balloon and artery wall, the film pressure remains sufficiently high that the medication will progressively proliferate through the arterial tissue. The pressure and flow will be continued for a predetermined time, for example, one to two minutes, as is sufficient to achieve the desired penetration of medication into the arterial wall. Preferably, the holes are placed so that the end most of the holes 29 are spaced inwardly somewhat from the conical ends of the balloon thereby defininq an annular portion at each end of the balloon which is unperforated and which may tend to have a partial sealing effect, tending to retard flow of the fluid from out between the balloon and the artery wall. The balloon then is deflated by aspirating through the inflation/deflation lumen to cause the balloon to collapse. The balloon catheter then is withdrawn from the patient. The flow area defined by the holes is sufficiently minute and the balloon wall is sufficiently flexible so that the balloon will collapse under aspiration.

By way of example, based on animal experiments conducted in accordance with the invention, the following penetrations of heparin through the tissue of an artery may be expected under the pressure levels for about one minutes.

| Gage Pressure at Proximal Part of Catheter | Estimated Average Pressure of Film in Contact with Artery | Depth of Penetration Into Wall of Artery in 1 Minute | Approximate Flow Rate of Unrestricted Catheter |
|---|---|---|---|
| 2 bar | 0–50 mm Hg | 100 microns | 2 cc/min |
| 3 bar | 150–300 mm Hg | 200 microns | 3 cc/min |
| 4 bar | 300–500 mm Hg | 300–400 microns | 4 cc/min |
| 5 bar | 500–1000 mm Hg | 500–700 microns | 5 cc/min |

Thus, we have described the invention by which highly concentrated medication may be applied to a surface of a body lumen, such as an artery, under sufficient pressure to cause the medication to penetrate into the tissue without introducing excessively high volumes of the medication into the patient's system. It should be understood, however, that although the invention has been described principally in connection with post-angioplasty treatment of an artery with heparin or an antiproliferative fraction of heparin, the invention may be practised in any instance where it is desired to apply a high concentration of medication to a local vessel or organ having a lumen accessible by a catheter. Thus the invention may be used to deliver chemotherapeutic drugs in the treatment of cancer patients where it is desired to apply concentrated medication or chemotherapeutic agents to the diseased organ. The catheter may be passed into a lumen in the organ or may even be inserted into a lumen formed in the organ or tumor for the express purpose of receiving the catheter. Therefore, it should be understood that other embodiments and modifications of the invention may be apparent to those skilled in the ar without departing from its spirit.

Having thus described the invention what we desire to claim and secure by Letters Patent is:

1. An apparatus for applying a liquid to a surface of the lumen of a body vessel and for effecting penetration of the liquid into the body vessel comprising:

a supporting member adapted to be inserted into the lumen of the body vessel;

a balloon mounted on the supporting member, the supporting member including an inflation lumen in communication with the interior of the balloon and having a portion adapted to be disposed outside of the patient;

the balloon being flexible and substantially inelastic and having a plurality of minute perforations in the form of about thirty holes substantially regularly spaced about the balloon and each having a diameter of the order of 25 microns adapted to provide a low, weeping flow rate of said liquid, said flow rate being no greater than a predetermined maximum flow rate when liquid in the balloon is under pressure;

said perforations defining a flow area sufficiently small so as not to adversely restrict the collapsing of the balloon about the support member under the influence of aspiration applied to the inflation lumen.

2. A catheter for applying a liquid to a surface of the lumen of a body vessel and for effecting penetration of the liquid into the body vessel comprising:

an elongated flexible shaft having a proximal end and a distal end and having an inflation lumen extending from its proximal toward its distal end;

a balloon mounted on the distal end of the shaft, the interior of the balloon being in communication with the inflation lumen, the balloon being flexible, and substantially inelastic, the balloon having a plurality of minute perforations in the form of about thirty holes substantially regularly spaced about the balloon and each having a diameter of the order of 25 microns adapted to provide a low, weeping flow rate of said liquid, said flow rate being no greater than a predetermined maximum flow rate when liquid in the balloon is under pressure;

said perforations defining a flow are sufficiently small so as not to adversely restrict collapsing of the balloon about the catheter shaft under the influence of aspiration applied to the inflation lumen.

3. A catheter as defined in claim 2 wherein the catheter is dimensioned and adapted to be percutaneously inserted and advanced into the coronary arteries.

4. A catheter for applying a liquid to a surface of the lumen of a body vessel and for effecting penetration of the liquid into the body vessel comprising:
an elongated flexible shaft having a proximal end and a distal end and having an inflation lumen extending from its proximal toward its distal end;
a balloon mounted on the distal end of the shaft, the interior of the balloon being in communication with the inflation lumen, the balloon being flexible, and substantially inelastic, the balloon having a plurality of minute perforations adapted to provide a low, weeping flow rate of said liquid, said flow rate being no greater than a predetermined maximum flow rate when liquid in the balloon is under pressure;
said perforations defining a flow area sufficiently small so as not to adversely restrict collapsing of the balloon about the catheter shaft under the influence of aspiration applied to the inflation lumen.

5. A catheter as defined in any one of claims 2 and 3 wherein the balloon includes a cylindrical perforated surface having an annular portion at each end that is free of perforations.

6. A catheter as defined in claim 4 wherein the wall thickness of the balloon is no greater than about 0.001".

7. A catheter as defined in claim 4 wherein the balloon is formed from polyethylene terephthalate.

8. A catheter as defined in claim 7 wherein the balloon includes a cylindrical perforated surface having an annular portion at each end that is free of perforations.

9. A catheter as defined in claim 6 wherein the balloon includes a cylindrical perforated surface having an annular portion at each end that is free of perforations.

10. A method for causing a liquid to penetrate tissue defining a body lumen comprising:
providing a catheter including an elongated flexible shaft having a proximal end and a distal end, the shaft having an inflation lumen extending from its proximal toward its distal end; a balloon mounted on the digital end of the shaft, the interior of the balloon being in communication with the lumen, the balloon being flexible and substantially inelastic, the balloon having a plurality of minute perforations adapted to provide a low, weeping flow rate of said liquid, said flow rate being no greater than a predetermined maximum flow rate when liquid in the balloon is under pressure; said perforations defining a flow area sufficiently small so as not to adversely restrict collapsing of the balloon about the catheter shaft under the influence of aspiration applied to the inflation lumen; the inflated diameter of the balloon being no less than the diameter of the body lumen;
inserting the catheter into the patient to locate the balloon in the lumen;
inflating the balloon in the body lumen so that it presses in intimate contact against the inner surface of the body lumen;
maintaining fluid pressure for a predetermined time to cause liquid to weep out of the holes in the balloon to form a thin film between the balloon and the lumen, the pressure level in the film being such as to force fluid to perfuse into the issue;
after a predetermined time, aspirating the balloon to deflate the balloon and remove the catheter.

11. A method as defined in claim 10 wherein the liquid is a concentrated medication and the pressure is not maintained beyond the time that the maximum amount of medication tolerable by the patient has wept through the balloon holes.

12. A method as defined in claim 10 wherein the body lumen is an artery and further comprising first performing an angioplasty in the artery and then performing the perfusion with said catheter, the balloon of the catheter being the same diameter as the balloon of the catheter that performed the angioplasty.

13. A method as defined in claim 12 wherein the perforated balloon is inflated with concentrated heparin solution.

14. An apparatus for applying a liquid to a surface of the lumen of a body vessel and for effecting penetration of the liquid into the body vessel comprising:
a supporting member adapted to be inserted into the lumen of the body vessel;
a balloon mounted on the supporting member, the supporting member including an inflation lumen in communication with the interior of the balloon and having a portion adapted to be disposed outside of the patient;
the balloon being flexible and substantially inelastic and having a plurality of minute perforations adapted to provide a low, weeping flow rate of said liquid, said flow rate being no greater than a predetermined maximum flow rate when liquid in the balloon is under pressure;
said perforations defining a flow area sufficiently small so as not t adversely restrict the collapsing of the balloon about the support member under the influence of aspiration applied to the inflation lumen.

15. A device as defined in claim 14 wherein said support member comprises a catheter and the balloon is mounted on the distal end of the catheter.

16. A device as defined in claim 14 wherein the wall thickness of the balloon is no greater than about 0.001".

17. A device as defined in claim 16 wherein the balloon is formed from polyethylene terephthalate.

18. A device as defined in any one of claims 14, 15, 16, 17 and 1 wherein the balloon includes a cylindrical perforated surface having an annular portion at each end that is free of perforations.

19. A method for causing a liquid to penetrate tissue defining a body lumen comprising:
providing a device including a support member, an inflation lumen and a balloon mounted on the support, the interior of the balloon being in communication with the lumen, the balloon being flexible and substantially inelastic, the balloon having a plurality of minute perforations adapted to provide a low, weeping flow rate of said liquid, said flow rate being no greater than a predetermined maximum flow rate when liquid in the balloon is under pressure;
said perforations defining a flow area sufficiently small so as not to adversely restrict collapse of the balloon on the support member under the influence of aspiration applied to the inflation lumen;
the inflated cross-sectional dimension of the balloon being no less than that of the body lumen;

inserting the device into the patient to locate the balloon in the body lumen;

inflating the balloon in the body lumen so that it presses in intimate contact against the inner surface of the body lumen;

maintaining fluid pressure for a predetermined time to cause liquid to weep out of the holes in the balloon to form a thin film between the balloon and the lumen, the pressure level in the film being such as to force fluid to perfuse into the tissue;

after a predetermined time, aspirating the balloon to deflate the balloon and remove the device.

20. A method as defined in claim 19 wherein the pressure is not maintained beyond the time that the maximum amount of medication tolerable by the patient has wept through the balloon holes.

21. A method for causing a liquid to penetrate tissue defining a body lumen comprising:

providing an applicator that includes a flexible, substantially inelastic balloon having a plurality of minute perforations adapted to provide a low, weeping flow rate of said liquid said flow rate being no greater than a predetermined maximum flow rate when liquid in the balloon is under pressure;

said perforations defining a flow area sufficiently small so as not to adversely restrict collapse of the balloon to a smaller configuration under the influence of aspiration applied to the balloon, the inflated diameter of the balloon being no less than the diameter of the body lumen;

inserting the balloon into the body lumen while in a deflated condition and then inflating the balloon so that it presses in intimate contact against the inner surface of the body lumen;

maintaining fluid pressure for predetermined time to cause liquid to weep out of the holes in the balloon to form a thin film between the balloon and the lumen, the pressure level in the film being such as to force fluid to perfuse into the tissue;

after a predetermined time, aspirating the balloon to reduce its size and then removing the balloon from the body lumen.

* * * * *

UNITED STATES PATENT AND TRADEMARK OFFICE
CERTIFICATE OF CORRECTION

PATENT NO. : 5,087,244

DATED : February 11, 1992

INVENTOR(S) : Harvey Wolinsky; Spencer B. King and Michael D. Barbare

It is certified that error appears in the above-identified patent and that said Letters Patent is hereby corrected as shown below:

Title Page: Item [75] "Spencer L. King" should read --Spencer B. King--.
Title Page: Item [56] after 1/1984 delete "Baron et al" and insert --Baran et al--.
Column 2, line 40, delete "defininq" and insert --defining--.
Column 5, line 3, delete "quiding" and insert --guiding--.
Column 5, line 5, delete "quidewire" and insert --guidewire--.
Column 5, line 14, delete "suqqested" and insert --suggested--.
Column 5, line 41, delete "defininq" and insert --defining--.
Column 6, line 23, delete "ar" and insert --art--.
Column 8, Claim 14, line 36, delete "t" and insert --to--.

Signed and Sealed this

Eighth Day of June, 1993

*Attest:*

MICHAEL K. KIRK

*Attesting Officer*     Acting Commissioner of Patents and Trademarks